US006853857B2

(12) United States Patent
Pfeiffer et al.

(10) Patent No.: US 6,853,857 B2
(45) Date of Patent: Feb. 8, 2005

(54) METHOD, DEVICE AND COMPUTER PROGRAM FOR DETERMINING THE BLOOD FLOW IN A TISSUE OR ORGAN REGION

(75) Inventors: Ulrich J. Pfeiffer, Munich (DE); Thorsten Burger, Munich (DE); Andreas Becker, Markt Schwaben (DE)

(73) Assignee: Pulsion Medical Systems AG, Munich (DE)

( * ) Notice: Subject to any disclaimer, the term of this patent is extended or adjusted under 35 U.S.C. 154(b) by 245 days.

(21) Appl. No.: 10/134,650

(22) Filed: Apr. 30, 2002

(65) Prior Publication Data

US 2002/0183621 A1 Dec. 5, 2002

(30) Foreign Application Priority Data

May 1, 2001 (DE) ........................................ 101 20 980

(51) Int. Cl.[7] .................................................. A61B 6/00
(52) U.S. Cl. ....................... 600/436; 600/407; 600/431; 600/419; 382/128; 382/130; 356/300; 356/302; 356/51; 356/39
(58) Field of Search ................................ 600/407, 473, 600/476, 481, 504, 310, 317, 319, 436, 419; 382/128, 130; 356/302, 300, 51, 39

(56) References Cited

U.S. PATENT DOCUMENTS 4,449,535 A  5/1984  Renault 5,074,306 A  12/1991 Green et al.
5,687,726 A  11/1997 Hoeft
5,865,757 A   2/1999 Hoeft
6,223,069 B1  4/2001 Pfeiffer et al.
6,549,801 B1 * 4/2003 Chen et al. .................. 600/425

FOREIGN PATENT DOCUMENTS

| DE | 32 10593 A1 | 10/1982 |
| DE | 41 30 931 A1 | 3/1993 |
| DE | 43 25 529 C2 | 2/1995 |
| WO | WO 96/16594 | 6/1996 |
| WO | WO 98/08434 | 5/1998 |

OTHER PUBLICATIONS

Joseph Still et al "Evaluation of the Circulation of Reconstructive Flaps Using Laser–Induced Fluorescence of Indocyanine Green" Annals of Plastic Surgery 42, 1999, pp. 266–274 (cited in specifications to be filed.

* cited by examiner

Primary Examiner—Brian L. Casler
Assistant Examiner—William Jung
(74) Attorney, Agent, or Firm—Nixon Peabody LLP; Donald R. Studebaker

(57) ABSTRACT

In a method, a device and a computer program for determining the blood flow in a tissue or organ region, the fluorescence intensity of an exogenous chromophore is measured as a function of time in the tissue region to be examined and from this the permeation rate of the chromophore is calculated, from which the blood flow can be derived.

65 Claims, 2 Drawing Sheets

METHOD, DEVICE AND COMPUTER PROGRAM FOR DETERMINING THE BLOOD FLOW IN A TISSUE OR ORGAN REGION

BACKGROUND OF THE INVENTION

The present invention relates to a method, a device and a computer program for determining the blood flow in a tissue or organ region.

A method for determining the depth of burns in tissue is known from U.S. Pat. No. 5,074,306, in which the fluorescence of the exogenous chromophore indocyanine green is detected and the depth of burn wounds is determined on the basis of its distribution in the tissue.

In "Annals of Plastic Surgery". 1999, Vol. 42, pp. 266–274 a device and a method for measuring the blood circulation through transferred skin flaps is described, wherein after applying indocyanine green the fluorescence stimulated by irradiation with a pulsed laser array is detected with a CCD camera.

In the case of the known methods and known devices only the relative fluorescence distribution of the chromophore indocyanine green in the tissue is examined qualitatively to establish the blood circulation through the tissue. The known methods are not suitable for determining the regional blood flow quantitatively on the basis of the fluorescence signal.

A method and a device for determining circulation through the brain and the intracranial blood volume is disclosed in WO 96/16594.

A method and arrangement for the non-invasive determination of cerebral blood flow by means of near infrared spectroscopy is known from WO 98/08434.

The methods of the two last-mentioned publications are based on the invasive or non-invasive spectroscopic measurement of the chromophore indocyanine green on the basis of its absorption behaviour in the near infrared spectral range. Moreover, these methods are not suitable for confining the tissue or organ region to be examined to a precisely defined area.

SUMMARY OF THE INVENTION

The object forming the basis of the invention is to provide a method, a device and a computer program, with the aid of which the blood flow in a precisely defined, possibly also extended, tissue or organ region can be determined with ease during routine application in the operating theatre.

A method for the non-invasive determination of the blood flow in a tissue or organ region is characterised by the steps:

(a) measurement of the fluorescence intensity of an exogenous chromophore as a function of time in the tissue or organ region after administration of the chromophore for the determination of a fluorescence curve f(t), (b) calculation of the permeation rate of the chromophore, (c) determination of the blood flow from the permeation rate.

It has been surprisingly found that the blood flow in a tissue or organ region can be determined with very high precision by calculating the permeation rate of a chromophore in conjunction with the measurement of the fluorescence intensity of an exogenous chromophore. In embodiments of the invention, an inadequate perfusion may be ascertained at an early stage during a surgical procedure, for example, and corrective measures can still be undertaken during the operation. The method can be used simply and without taking a great deal of time during an operation for the qualitative indication and for quantification of the blood flow in a precisely defined tissue region. In this case, a complete perfusion indication can be conducted in two minutes.

It follows from this that the method may also be used during an operation without hindering the procedure during the operation. The invention allows the perfusion to be recorded in real time in digital form, and if desired also in the form of a video image sequence. A quantitative evaluation is also possible in conjunction with the use of an evaluator unit.

Assessment of the tissue perfusion can be improved by comparative measurements in several tissue or organ regions.

According to an advantageous embodiment of the invention, after administration of the chromophore the tissue or organ region is irradiated with a radiation source, as a result of which the chromophore is stimulated to fluorescence. The radiation emission of the fluorescing chromophore is detected. Since the emission caused by the fluorescence occurs in a spectral range which differs from the spectral range of the stimulation of the chromophore, it is assured during measurement of the fluorescence intensity in the tissue or organ region to be examined that the fluorescent emission of the chromophore alone is detected, while detection of the stimulating radiation is excluded.

According to a further aspect of the invention, the blood flow in the tissue or organ region to be examined is determined from the permeation rate of the chromophore. It has been proved that as a result of this a reliable indication regarding the blood flow in the tissue or organ region is possible especially in the case of measurements of fluorescence in contrast to the known methods, in which only the static distribution of the chromophore is determined by measuring fluorescence.

An increase in precision of the blood flow measurement in a tissue or organ region can be achieved according to an advantageous embodiment of the invention in that the permeation rate is calculated from the rise of the transport function of the vascular system determining the blood flow in the tissue or organ region. The transport function is to a certain extent the response function of the system which would bring the system to a pulse-type stimulation.

Since pulse-type stimulation is not possible in practice, the transport function g(t), according to a further advantageous embodiment of the invention, is determined by a mathematical deconvolution of the measured fluorescence curve. For this, the time curve of the chromophore density a(t) is determined at an artery upstream of the tissue or organ region. The transport function g(t) is determined by a variation method so that the term $$f(t) - \int_{-\infty}^{+\infty} g(t-u) a(u) du]^2$$

becomes a minimum.

The efficiency of modern computers makes it possible to determine the appropriate transport function g(t), which makes the said term a minimum, within a very short time.

According to an advantageous further development of the invention, a fluorescent dye with at least one fluorescence maximum in the near infrared wavelength range is used as chromophore. Further advantageous properties of the chromophore are that it remains within the vascular system after administration and is broken down by the body within a few minutes, as a result of which repeat measurements are possible. Indocyanine green has proved to be particularly advantageous as chromophore for this purpose.

According to a further aspect of the invention, a device for determining the blood flow in a tissue or organ region can comprise an irradiation unit for irradiation of the tissue or organ region with electromagnetic radiation in a specific spectral range, a detector unit for measurement of a fluorescent intensity of a fluorescing chromophore in the tissue or organ region for determination of a fluorescence curve f(t), and an arithmetic unit, which calculates the permeation rate of the chromophore by evaluation of the fluorescence curve and determines the blood flow from the calculated permeation rate.

According to an advantageous embodiment, the detector unit is an imaging unit, which enables at least one image area to be defined as a measurement region and at least one image area to be defined as a reference region. To determine the fluorescence curve, more precisely the fluorescence curves, only the defined areas are used. The fluorescence curve of the measurement region is correlated with the fluorescence curve of the reference region. Random disturbances such as fluctuations in chromophore concentration, for example, can be eliminated during calculation of the blood flow by forming the difference or the relation of the two curves.

It can be provided that the arithmetic unit determines the permeation rate from the steepness of the rise of the fluorescence curve, or—according to a preferred embodiment—that the arithmetic unit for calculation of the permeation rate calculates the transport function g(t) of the vascular system decisive for the blood flow in the tissue or organ region by mathematical deconvolution and determines the permeation rate from the steepness of the rise of the transport function g(t).

The radiation source is preferably selected so that it emits precisely in the spectral range of the fluorescence stimulation of the chromophore. In contrast, the detector unit is set to the spectral range of the fluorescent emission of the chromophore, e.g. by using filters, thus assuring that only fluorescent radiation and not stimulating radiation, for instance, passes into the detector unit.

According to a further aspect of the invention, this also relates to a computer program, in particular a computer program recorded on a storage medium, which is to be loaded into the program memory of a computer and causes the computer to execute the following steps:
  (a) generation of sample values of a fluorescence curve f(t) working from fluorescence intensity measured values made available at an input of the computer,
  (b) calculation of the permeation rate of a chromophore from the sample values of the fluorescence curve.

With the assistance of the program a quantitative value regarding the blood flow in the tissue or organ region to be examined can be determined in a very short time during a surgical procedure, for example. According to a first embodiment of the computer program, the permeation rate is determined from the rise of the fluorescence curve.

According to an advantageous further development of the computer program, this has a program module which enables the selection of at least one measurement region and at least one reference region within the image recorded by the video camera. For evaluation, the fluorescence curve of the measurement region is correlated with the fluorescence curve of the reference region. Random disturbances such as fluctuations in chromophore concentration, for example, can be eliminated during calculation of the blood flow by forming the difference or the relation of the two curves.

However, an increased measurement precision results according to a particular variant of the computer program, in which the permeation rate is determined from the rise of the transport function of the vascular system determining the blood flow in the tissue or organ region. In this case, a more precise quantitative indication regarding the blood flow is possible, in particular in cases where the chromophore cannot be administered in a "pulse-type" manner. For this, it is provided according to a particular embodiment of the computer program according to the invention that the transport function g(t) is determined by mathematical deconvolution as a result of
  (a) sample values of the time curve of the chromophore density a(t) being determined at an artery upstream of the tissue or organ region working from chromophore density measured values made available at an input of the computer, and
  (b) the transport function g(t) being determined by variation so that the term $$\left[f(t) - \int_{-\infty}^{+\infty} g(t-u)a(u)\,du\right]^2$$

assumes a minimum.

The method according to the invention, the device according to the invention and the computer program according to the invention are particularly suitable for use where the quantification of circulation through tissue can be decisive during surgery, i.e. in the field of visceral surgery in left-side colon and rectum resections, in stomach section transposition after oesophagus resection, in free small intestine transplants for interposition as well as in all Roux' Y reconstructions (after gastrectomy, as bilio-digestive anastomoses etc.). The invention is also suitable for the detection of secondary perfusion disorders in the case of strangulated hernia or bridenileus. In heart surgery the invention can be used to examine the efficiency of coronary bypasses. In the field of plastic surgery it is possible to monitor the perfusion of transferred skin flaps as well as to assess tissue damage in the case of traumas (e.g. fractures of the navicular bone, comminuted fractures, soft tissue injuries as well as gunshot wounds).

BRIEF DESCRIPTION OF THE DRAWINGS

The invention is explained in more detail below on the basis of an embodiment shown in the drawings.

DESCRIPTION OF THE PREFERRED EMBODIMENTS

Figure 1:
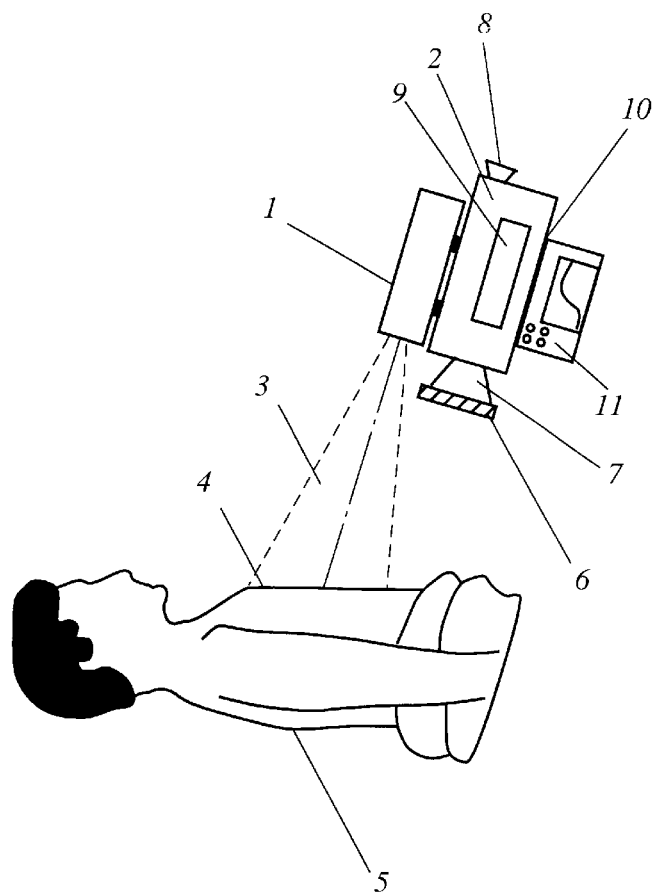
FIG. 1 shows the schematic arrangement of a device according to the invention in use during an operation.

Referring to the drawings, FIG. 1 schematically shows a device according to the invention in use during an operation in a view not to scale. A safety case 1, into which an infrared laser light source with a peak emission of 780 nm is integrated, together with a CCD camera 2 and an arithmetic or evaluator unit 11, forms a compact unit, which can be carried and operated with one hand, has an accumulator and is therefore usable independently of mains power.

The expanded laser light 3 discharging from the safety case 1 has a surface intensity of less than 1 mW/cm$^2$ and lies below the limit value of the maximum permitted irradiation of the cornea of the eye, and as a result no safety glasses need to be worn in the vicinity of the device.

The expanded beam bundle 3 of the infrared laser light source irradiates the approximately 30 cm wide field of operation 4, which is located approximately at a distance of 70 cm from the safety case 1. Indocyanine green previously administered to the patient 5 in a dose of 0.1 to 2 mg per kg body weight is stimulated to fluorescence by the irradiation.

The fluorescence signal is detected by the CCD camera 2, which is sensitive in the near infrared wavelength range, connected upline of a filter 6. The filter 6 is an NIR long-wave pass filter (sharp cut-off filter), which is only capable of transmitting wavelengths higher than 800 nm and is screw-connected to the autofocus lens 7 of the CCD camera 2 by means of an external thread. Alternatively, a filter, which enables a narrow-band transmission in the range of the fluorescence peak of the chromophore indocyanine green, is also suitable. The CCD camera 2 has a viewfinder 8, and therefore no external monitor needs to be used during the operation and thus a cable connection, which may possibly hinder handling, is unnecessary. The electronic image data of the detected fluorescence are digitally recorded on a video cassette 9.

A sterile cloth (not shown) may be disposed between the patient 5 and the unit comprising CCD camera 2 and safety case 1, so that the device itself does not need to be sterile. Because of the compact construction and the absence of cable connections, the unit comprising CCD camera 2 and safety case 1 can, however, also be easily sterile packed.

Via an interface 10 in accordance with IEEE 1394, which enables a data transfer rate of up to 400 MBit/s, an electronic image processing and evaluation system 11 can be connected to the CCD camera 2, which allows the brightness of the individual picture elements (pixels) to be mapped quantitatively as measure for the fluorescent intensity. For this, different image areas can be marked by the user on the first image of an image sequence in order to then determine the brightness of the pixels in this area image by image and graphically represent the results. In this case, a tissue or organ region to be examined can be compared directly with a reference area with normal perfusion or with an external standard of known intensity. When using an external standard, image sequences recorded with different irradiation or detector parameters may also be compared directly with one another. By evaluation of the entire image sequence it is possible to apply various criteria such as the rate of permeation and flow-off of the chromophore and the change in fluorescent intensity in the tissue areas caused by the chromophore, for example, for the evaluation.

Figure 2:
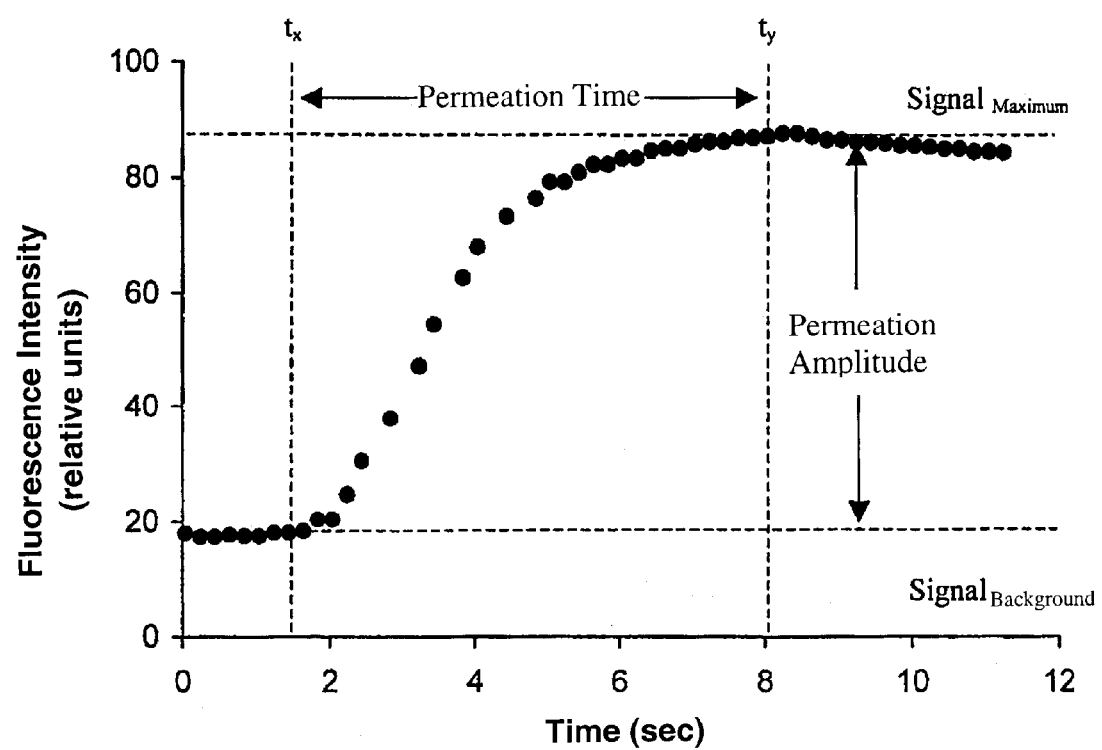
FIG. 2 is a graph representing the fluorescence intensity as a function of time.

FIG. 2 shows the fluorescence intensity (measured in relative units from 0–100) as a function of time (measured in seconds) in a graph. It may be seen that the curve of the fluorescence intensity starts from a background signal of 20 unit and from the time $t_x$ rapidly rises until the signal maximum is reached at time $t_y$ (8 seconds). After this, the fluorescence intensity remains constant and later slowly drops. The period of time between times $t_x$ and $t_y$, which can be designated as the permeation time, allows the blood flow in the examined tissue or organ region to be calculated. This means that the blood flow is greater, the shorter the permeation time and hence the steeper the course of the fluorescence curve.

A transport function can be obtained from the fluorescence curve, which directly indicates the measured fluorescence intensity as a function of time, by means of mathematical deconvolution. The transport function corresponds to a theoretical fluorescence curve, which would have been obtained if the chromophore had been administered fully at a single point in time (without time extension). Therefore, by calculating the transport function all contingencies occurring in practice caused as a result of the chromophore not being administered in sudden bursts but slowly over a longer period of time are excluded. The transport function obtained by deconvolution qualitatively exhibits the same course as the fluorescence curve shown in FIG. 2, but runs slightly more steeply.

Figure 3:
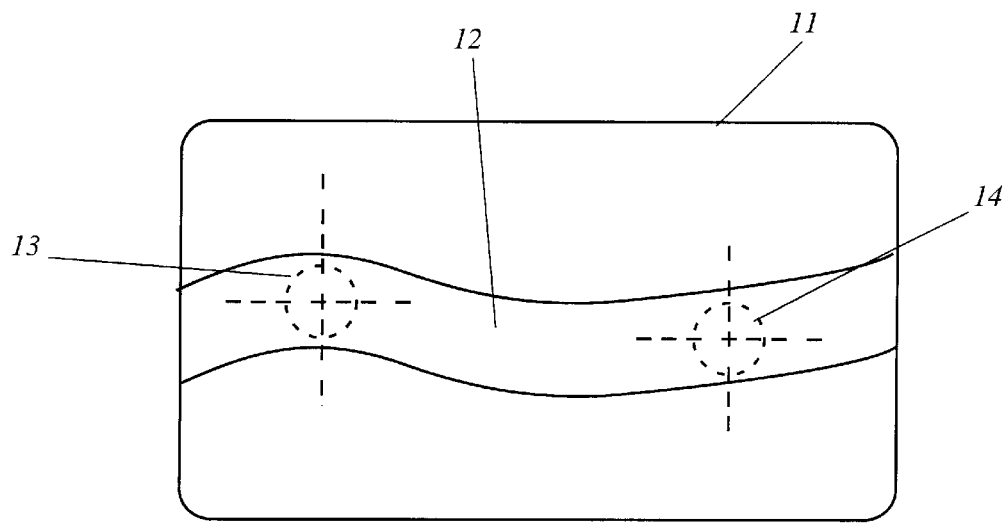
FIG. 3 shows a viewfinder image of a camera used in association with the invention.

FIG. 3 shows a viewfinder image of the camera used as detector unit in embodiments of the invention. A stomach section to be transposed for replacement of the oesophagus is shown schematically in the centre of the viewfinder image. Two target graticules 13 and 14 can be directed to specific regions of interest within the viewfinder image via control knobs (not shown). Target graticule 13, for example, is directed to a location for transposition which is particularly critical with respect to circulation, whereas target graticule 14 is directed to a location for transposition where good circulation is assured. During operation of the detector unit 2 only the picture elements (pixels) within the regions selected by the graticules are evaluated, i.e. the region in the target graticule 13 as measurement region and the region in the target graticule 14 as reference region. In this way, the blood flow in the measurement region of the target graticule 13 can be determined quantitatively, in which case contingencies such as fluctuations in chromophore concentration etc., for example, are eliminated by formation of a difference to the measurement in the reference region.

It will be understood that the above description of the present invention is susceptible to various modifications, changes and adaptations.

What is claimed is:

1. A method for determining the blood flow in a tissue or organ region including the following steps:
   (a) determination of a fluorescence curve f(t) by measurement of the fluorescence intensity of an exogenous chromophore as a function of time in the tissue or organ region after administration of the chromophore,
   (b) calculation of the permeation rate of the chromophore,
   (c) determination of the blood flow from the permeation rate, wherein the calculated permeation rate is correlated with the measurement results of a parallel measurement of a reference region.

2. A method according to claim 1, wherein for the fluorescence measurement the tissue or organ region is irradiated with a radiation source and the emission of radiation is detected in a fluorescence spectral range of the chromophore.

3. A method according to claim 2, wherein said radiation source emits in the infrared spectral range.

4. A method according to claim 2, wherein said radiation source emits in a spectral range differing from said fluorescence spectral range.

5. A method according to claim 1, wherein said permeation rate is determined from the rise of said fluorescence intensity of said chromophore.

6. A method according to claim 1, wherein there is a vascular system determining the blood flow in the tissue or organ region and having a transport function g(t), and said permeation rate is calculated from the rise of said transport function.

7. A method according to claim 6, wherein said transport function g(t) is determined by mathematical deconvolution as a result of (a) the time curve of the chromophore density a(t) being determined at an artery upstream of the tissue or organ region, and (b) said transport function g(t) being determined so that the term $$\left[f(t) - \int_{-\infty}^{+\infty} g(t-u)a(u)\,du\right]^2$$

assumes a minimum.

8. A method according to claim 1, wherein for measurement of said fluorescence intensity of said exogenous chromophore a fluorescence signal is recorded with a digital video camera.

9. A method according to claim 8, wherein said video camera generates an image, and said measurement region and said reference region are selected in said image, and a fluorescence signal of said measurement region is correlated with a fluorescence signal in said reference region.

10. A method according to claim 1, wherein a fluorescent dye with at least one fluorescence maximum in the near infrared wavelength rang is used as said chromophore.

11. A method according to claim 10, wherein indocyanine green ($C_{13}H_{47}N_2NaO_6S_2$) is used as said chromophore.

12. A method according to claim 11, wherein indocyanine green is applied in a dose which excludes fluorescence quenching effects.

13. A method according to claim 12, wherein indocyanine green applied in a dose of <10 $\mu$M is used as said chromophore.

14. A method for determining the blood flow in a tissue or organ region including the following steps:

(a) determination of a fluorescence curve f(t) by measurement of the fluorescence intensity of an exogenous chromophore as a function of time in the tissue or organ region after administration of the chromophore, (b) calculation of the permeation rate of the chromophore, (c) determination of the blood flow from the permeation rate, wherein the calculated permeation rate is correlated with the measurement results of a parallel measurement of an external reference standard.

15. A method according to claim 14, wherein for the fluorescence measurement the tissue or organ region is irradiated with a radiation source and the emission of radiation is detected in a fluorescence spectral range of the chromophore.

16. A method according to claim 15, wherein said radiation source emits in the infrared spectral range.

17. A method according to claim 15, wherein said radiation source emits in a spectral range differing from said fluorescence spectral range.

18. A method according to claim 14, wherein said permeation rate is determined from the rise of said fluorescence intensity of said chromophore.

19. A method according to claim 14, wherein there is vascular system determining the blood flow in the tissue or organ region and having a transport function g(t), and said permeation rate is calculated from the rise of said transport function.

20. A method according to claim 19, wherein said transport function g(t) is determined by mathematical deconvolution as a result of (a) the time curve of the chromophore density a(t) being determined at an artery upstream of the tissue or organ region, and (c) said transport function g(t) being determined so that the term $$f(t) - \int_{-\infty}^{+\infty} g(t-u)a(u)\,du]^2$$

assumes a minimum.

21. A method according to claim 14, wherein for measurement of said fluorescence intensity of said exogenous chromophore a fluorescence signal is recorded with a digital video camera.

22. A method according to claim 14, wherein a fluorescent dye with at least one fluorescence maximum in the near infrared wavelength range is used as said chromophore.

23. A method according to claim 22, wherein indocyanine green ($C_{13}H_{47}N_2NaO_6S_2$) is used as said chromophore.

24. A method according to claim 23, wherein indocyanine green is applied in a dose which excludes fluorescence quenching effects.

25. A method according to claim 24, wherein indocyanine green applied in a dose of <10 $\mu$M is used as said chromophore.

26. A device for determining the blood flow in a tissue or organ region including:

(a) an irradiation unit for irradiation of the tissue or organ region with electromagnetic radiation in a specific spectral range, (b) a detector unit for measurement of a fluorescence intensity of a fluorescing chromophore in the tissue or organ region for determination of a fluorescence curve f(t), (c) an arithmetic unit, which calculates the permeation rate of the chromophore by evaluation of the fluorescence curve and determines the blood flow from the calculated permeation rate, wherein said detector unit comprises an imaging device, and wherein there is provided a selector unit for selecting at least one measurement region and at least one reference region in an image generated by the imaging device, and in the determination of blood flow, said arithmetic unit relates the permeation rate to the results of a parallel measurement in said reference region.

27. A device according to claim 26, wherein said imaging device is a digital camera.

28. A device according to claim 27, wherein said digital camera is designed to record a video image sequence of the tissue or organ region.

29. A device according to claim 26, wherein said arithmetic unit determines the permeation rate from the steepness of the rise of the fluorescence curve f(t).

30. A device according to claim 26, wherein there is a vascular system decisive for the blood flow in the tissue or organ region and having a transport function g(t), said arithmetic unit calculating said transport fraction by mathematical deconvolution and determines the permeation rate from the steepness of the rise of the transport function g(t).

31. A device according to claim 26, wherein said radiation unit emits radiation in the spectral range of the absorption maximum of said chromophore.

32. A device according to claim 26, wherein said radiation unit is a light-emitting diode unit with bundled emission.

33. A device according to claim 26, wherein said radiation unit is an infrared laser light source.

34. A device according to claim 26, wherein said radiation unit is a laser diode.

35. A device according to claim 26, wherein said radiation unit is pulsed.

36. A device according to claim 26, wherein said radiation unit is modulated.

37. A device according to claim 26, wherein said radiation unit has a surface intensity of less than 1 mW/cm² and is not dangerous to the unprotected human eye.

38. A device according to claim 26, wherein said radiation unit emits in the spectral range around 805 nm.

39. A device according to claim 26, wherein said detector unit detects radiation in the range of the fluorescent wavelength of said chromophore.

40. A device according to claim 26, wherein said detector unit detects radiation in the range of 835 nm.

41. A device according to claim 26, and constructed as a compact unit.

42. A device for determining the blood flow in a tissue or organ region including:
(a) an irradiation unit for irradiation of the tissue or organ region with electromagnetic radiation in a specific spectral range,
(b) a detector unit for measurement of a fluorescence intensity of a fluorescing chromophore in the tissue or organ region for determination of a fluorescence curve f(t),
(c) an arithmetic unit, which calculates the permeation rate of the chromophore by evaluation of the fluorescence curve and determines the blood flow from the calculated permeation rate,
wherein said detector unit comprises an imaging device, and wherein there is provided a selector unit for selecting at least one measurement region in an image generated by the imaging device, and in the determination of blood flow, said arithmetic unit relates the permeation rate to the results of an external standard measurement.

43. A device according to claim 42, wherein said imaging device is a digital camera.

44. A device according to claim 43, wherein said digital camera is designed to record a video image sequence of the tissue or organ region.

45. A device according to claim 42, wherein said arithmetic unit determines the permeation rate from the steepness of the rise of the fluorescence curve f(t).

46. A device according to claim 42, wherein there is a vascular system decisive for the blood flow in the tissue or organ region and having a transport function g(t), said arithmetic unit calculating said transport function by mathematical deconvolution and determines the permeation rate from the steepness of the rise of the transport function g(t).

47. A device according to claim 42, wherein said radiation unit emits radiation in the spectral range of the absorption maximum of said chromophore.

48. A device according to claim 42, wherein said radiation unit is a light-emitting diode unit with bundled emission.

49. A device according to claim 42, wherein said radiation unit is an infrared laser light source.

50. A device according to claim 42, wherein said radiation unit is a laser diode.

51. A device according to claim 42, wherein said radiation unit is pulsed.

52. A device according to claim 42, wherein said radiation unit is modulated.

53. A device according to claim 42, wherein said radiation unit has a surface intensity of less than 1 mW/cm² and is not dangerous to the unprotected human eye.

54. A device according to claim 42, wherein said radiation unit emits in the spectral range around 805 nm.

55. A device according to claim 42, wherein said detector unit detects radiation in the range of the fluorescent wavelength of said chromophore.

56. A device according to claim 42, wherein said detector unit detects radiation in the range of 835 nm.

57. A device according to claim 42 and constructed as a compact unit.

58. A computer program, encoded on a computer-readable medium having a computer program recorded thereon and arranged to be loaded into a program memory of a computer and to cause the computer to execute the following steps:
(a) generation of sample values of a fluorescence curve f(t) based on fluorescence intensity measured values made available at an input of the computer,
(b) calculation of the permeation rate of a chromophore from the sample values of the fluorescence curve f(t), wherein said computer program further has a program module for the selection of at least one reference region, and wherein step (b) includes a comparison with the permeation rate determined in said reference region.

59. A computer program according to claim 58, wherein said permeation rate is determined from the rise of said fluorescence curve f(t).

60. A computer program according to claim 58, wherein there is a vascular system, determining the blood flow in the tissue or organ region and having a transport function g(t) and said permeation rate is determined from the rise of said transport function.

61. A computer program according to claim 60, wherein said transport function g(t) is determined by mathematical deconvolution as a result of
(a) sample values of the time curve of the chromophore density a(t) being determined at an artery upstream of the tissue or organ region based on chromophore density measured values made available at an input of the computer, and
(b) said transport function g(t) being determined so that the term $$\left[ f(t) - \int_{-\infty}^{+\infty} g(t-u)a(u)\,du \right]^2$$

assumes a minimum.

62. A computer program, encoded on a computer-readable medium having a computer program recorded thereon and arranged to be loaded into a program memory of a computer and to cause the computer to execute the following steps:
(a) generation of sample values of a fluorescence curve f(t) based on fluorescence intensity measured values made available at an input of the computer,
(b) calculation of the permeation rate of a chromophore from the sample values of the fluorescence curve f(t), wherein step (b) includes a comparison with the permeation rate determined in an external standard.

63. A computer program according to claim 62, wherein said permeation rate is determined from the rise of said fluorescence curve f(t).

64. A computer program according to claim 62, wherein here is a vascular system, determining the blood flow in the tissue or organ region and having a transport function g(t) and said permeation rate is determined from the rise of said transport function.

65. A computer program according to claim 64, wherein said transport function g(t) is determined by mathematical deconvolution as a result of
(a) sample values of the time curve of the chromophore density a(t) being determined at an artery upstream of the tissue or organ region based on chromophore density measured values made available at an input of the computer, and (b) said transport function g(t) being determined so that the term $$\left[ f(t) - \int_{-\infty}^{+\infty} g(t-u)a(u)\,du \right]^2$$

assumes a minimum.

* * * * *